United States Patent [19]
Yue

[11] Patent Number: 6,007,536
[45] Date of Patent: Dec. 28, 1999

[54] VARIABLE ANGLE BLADE PLATE FOR FIXATION OF CANCELLOUS BONE

[76] Inventor: James J. Yue, 814 Fernwood Rd., Moorestown, N.J. 08057

[21] Appl. No.: 09/200,930

[22] Filed: Nov. 30, 1998

[51] Int. Cl.[6] .................................................. A61B 17/56
[52] U.S. Cl. .............................................. 606/60; 606/71
[58] Field of Search ................................. 606/71, 70, 69, 606/61, 60, 101

[56] References Cited

U.S. PATENT DOCUMENTS

| | | | |
|---|---|---|---|
| 5,674,222 | 10/1997 | Berger et al. ............................. | 606/69 |
| 5,810,822 | 9/1998 | Mortier .................................... | 606/69 |

OTHER PUBLICATIONS

Biomet Inc., "ari–Angle Hip System", Technique Manual, Warsaw Indiana, pp. 1–7, 1998.

M. E. Müller et al., "Manual of Internal Fixation: Techniques Recommended by the AO–ASIF Group, 3rd Edition", Springer Verlag, Berlin, pp. 252–265, 1991.

Aaron A. Hofmann et al., "High Tibial Osteotomy", *Clinical Orthopaedics*, pp. 212–217, 1991.

T. Koshino et al., "High Tibial Osteotomy with Fixation by a Blade Plate for Medial Compartment Osteoarthritis of the Knee", *Orthop Clin North Am.*, 20(2), pp. 227–243, 1989.

Andrew M. Wolff, M.D. et al., "The Treatment of nonunion of proximal tibial osteotomy with internal fixation", *Clin Orthop*, 250, pp. 207–215k, 1990.

Kazunori Yasuda, M.D. et al., "A Ten–to 15–year Follow–Up Observation of High Tibial Osteotomy in Medial Compartment Osteoarthrosis", *Clin Orthop*, 282, pp. 186–195, 1992.

*Primary Examiner*—Michael Buiz
*Assistant Examiner*—Jonathan D. Goldberg
*Attorney, Agent, or Firm*—Sughrue, Mion, Zinn, Macpeak & Seas, PLLC

[57] ABSTRACT

An orthopedic plate for treating orthopedic peri-articular fractures and osteotomies, including a flat and curve edged blade for insertion into the spongy or cancellous bone to gain fixation, a side plate portion which includes a plurality of screw holes, the side plate portion fixing the plate to the bone when screws are inserted in the screw holes, and a worm gear mechanism which connects the blade and the side plate portion, and which allows for variable angles between the blade and the side plate portion to overcome problems associated with fracture and osteotomy orientation and rigid fixation in cancellous bone in the metaphyseal portion of long bones such as the shoulder, knee, ankle, and hip, and thus, greatly facilitate the proper fixation and alignment for peri-articular fractures.

15 Claims, 4 Drawing Sheets

PRIOR ART

VARIABLE ANGLE BLADE PLATE FOR FIXATION OF CANCELLOUS BONE

The present invention relates to a variable angle blade plate for the fixation of spongy or cancellous bone, which allows for variable angles which may be subtended as a result of a given bone anatomy.

BACKGROUND OF THE INVENTION

1. Field of the Invention

The present invention is related to an orthopedic surgical implant for bone stabilization of peri-articular fractures, peri-articular osteotomies, and other orthopedic procedures involving periarticular regions.

Stable fixation in spongy or cancellous bone is, at times, a difficult problem in the field of orthopedic surgery, especially in orthopedic trauma and orthopedic osteotomy surgery. Often comminuted and geriatric/osteoporotic bone is difficult to stabilize with conventional screw and plate fixation. An equally difficult problem pertains to the placement of two large bone fragments in their proper sagittal and coronal orientation when performing orthopedic osteotomies.

2. Description of the Related Art

A procedure which is used commonly to treat early arthritis of the knee is the peri-articular valgus osteotomy. This osteotomy takes a "bow legged" deformity and creates a partial "knock kneed" deformity in order to transfer the weight off of the inner arthritic compartment of the knee onto the outer non-arthritic compartment of the knee. The average period of pain relief and maintenance of the knock kneed alignment is 5–7 years; at which time, the patient is left to live with his or her pain or depending on their age, may elect to have a total knee replacement. The fixation of these types of osteotomies has been commonly done with one piece plates, staples, and one piece blade plates.

These fixation systems are limited by their one piece solid designs and do not allow for small corrections which may be necessary because of anatomic variation. Even the correction of a few degrees of alignment may mean the difference between 5 years of pain relief and a lifetime of pain relief without the need for a second procedure.

The fixation of fractures, delayed unions, and non-unions in close proximity to the hip, knee, shoulder and ankle joints often poses similar and sometimes more troublesome problems as compared to peri-articular osteotomies. Fractures which occur in the elderly are often difficult to treat because of the osteoporotic nature of their bone.

Conventional plates rely on screw fixation into bone to secure the plate to the outside of the bone. The use of a blade plate attempts to overcome this lack of fixation. However, the proper placement of this blade plate is essential to return the normal anatomic alignment of the limb. It is often difficult to judge this placement because of the shattered bone fragments which accompany the fracture.

The conventional one piece blade plates, shown in FIG. 4, are constructed of a single piece of metal at fixed angles, but are without the ability to compensate for variations in bony anatomy. Therefore, even when precise placement of these plates is achieved when used for fracture fixation and periarticular osteotomies, the overall alignment of the limb may not be optimum because of the one piece fixed angled plate.

Although conventional two piece variable angle screw devices exist, they are currently used in hip fractures. These variable angle screw devices include a compression screw inserted into the femoral cortex, and include adjusting the angle of the device before screwing the plate into and flush with the femur, as shown in FIG. 5. However, this system does not allow for the treatment of metaphyseal fractures or osteotomies of the hip, knee, ankle, or shoulder by virtue of its inherent configuration.

SUMMARY OF THE INVENTION

The variable angle blade plate of the present invention has been designed to overcome problems associated with fracture and osteotomy orientation and rigid fixation in cancellous bone in the metaphyseal portion of long bones such as the shoulder, knee, ankle, and hip, and thus, greatly facilitate the proper fixation and alignment for peri-articular fractures.

The present invention uses the concept of blade plate fixation and variable angle plate fixation to achieve these goals. The second embodiment, which includes a double blade, allows for the elevation and support of those fractures that have a split and depressed pattern.

Specifically, the present invention comprises a metal plate whose proximal or top end is fashioned to gain fixation in cancellous or spongy bone by virtue of its flat shape and slightly curved edges. The distal or bottom portion of the plate is applied to the distal bone with screws. An interposed worm screw mechanism between the top and bottom of the plate allows for variable angles which may be subtended as a result of a given bone anatomy.

In a first embodiment of the present invention, the blade portion of the variable angle blade plate is made of a single blade. This single blade configuration would be used for osteotomies and fractures of the proximal tibia.

In a second embodiment of the present invention, the blade portion is comprised of two blades each connected to the side plate by a separate worm screw mechanism. This double blade configuration would be used to treat more complex fractures which have split and depressed fragments of bone that require elevation and support.

DETAILED DESCRIPTION OF THE PREFERRED EMBODIMENTS

The variable angle blade plate is used in the treatment of peri-articular fractures and osteotomies of the hip, knee, ankle, and shoulder. Depending on which of these bones is under consideration, an appropriately sized and contoured variable angle blade plate is chosen. Due to the fact that each bone has a given size, the variable angle blade plate should be made in appropriately sized and contoured blades, side plates, and worm gear mechanisms.

Figures 1A, 1B:
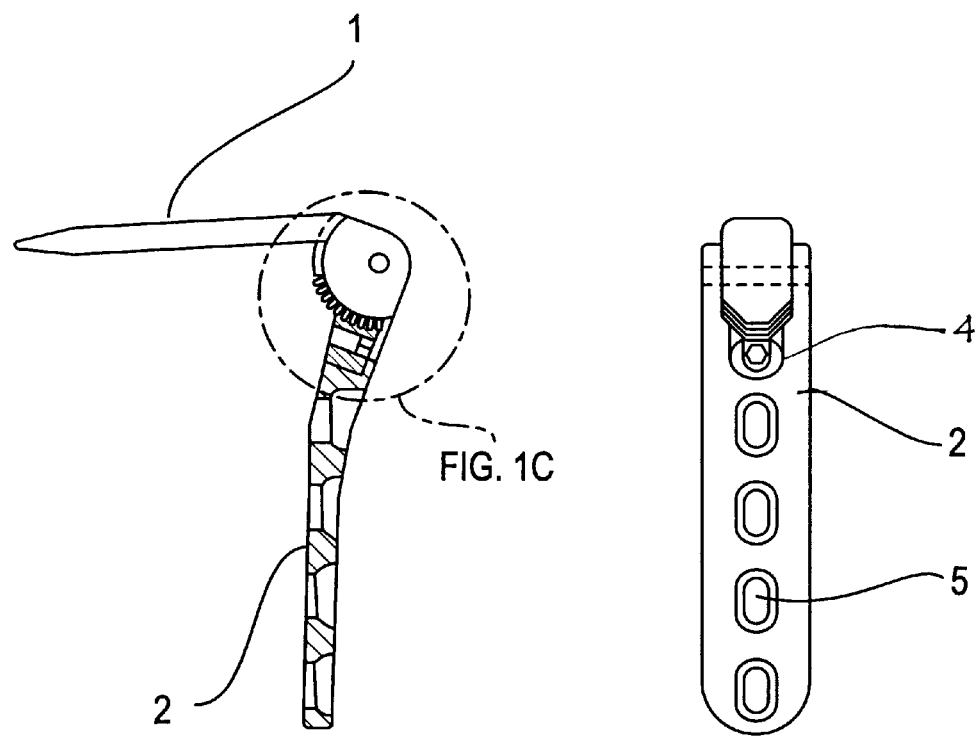
FIG. 1A shows a side view of the variable angle blade plate with the worm gear mechanism.
FIG. 1B shows a front view of side plate portion of the variable angle blade plate.

The first embodiment of the invention is shown in FIGS. 1A–1C and 2, and is a single blade variable angle blade plate. FIG. 1A is a side view of the variable angle blade plate as if it were lying on edge similar to a ruler resting on its thinner edge on a table. The blade portion 1 has a tapered distal end which is inserted into the bone. The blade portion 1 is normally made of metal, and is fashioned to gain fixation in cancellous or spongy bone by virtue of its flat shape and slightly curved edges.

Figure 1C:
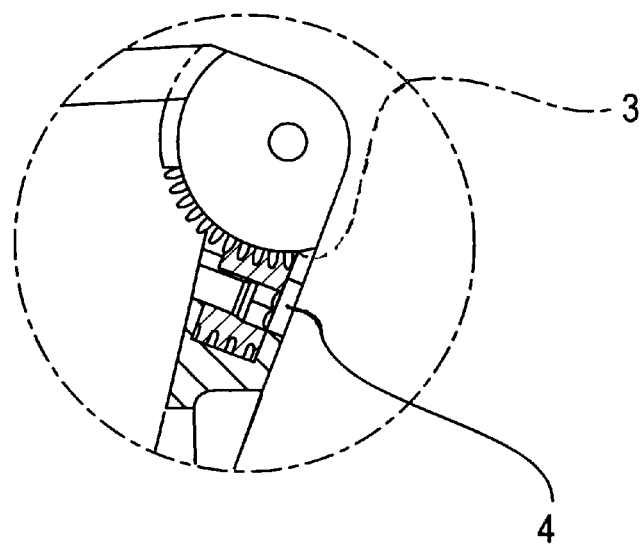
FIG. 1C shows an enlarged view of the worm gear mechanism of the variable angle blade plate.

The worm gear mechanism 3, which is shown in more detail in FIG. 1C, allows the angle of the plate to be adjusted prior to the side plate portion 2 of the plate being screwed into the bone. A worm gear adjustment portion 4, which consists of an open hexagonal screw head, permits the placement of a screw driver in the worm gear mechanism 3 to turn the worm gear and change the angle of the blade portion 1 relative to the side plate portion 2. Screw holes 5 are disposed in the side plate portion 2 to allow screws 6 to be inserted into the side plate portion 2 and fix the side plate portion 2 flush to the bone after adjustment of the worm gear mechanism 3.

FIG. 1B shows the variable angle blade plate in a front view, wherein the plate is resting on its more broad surface similar to a ruler resting on a table on its wider surface. FIG. 1B more clearly shows the worm gear adjustment portion 4 and the screw holes 5.

Figure 2:
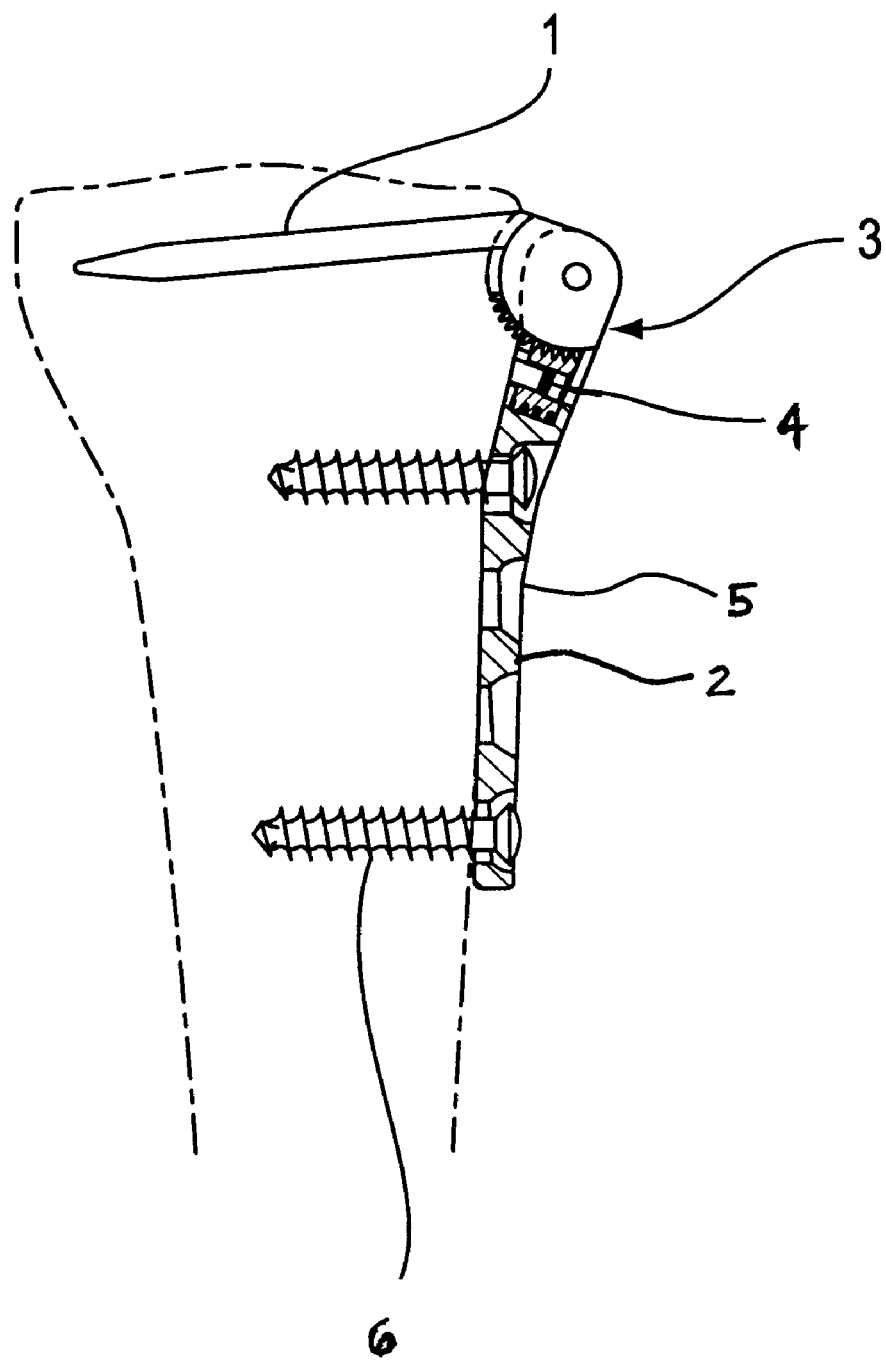
FIG. 2 shows a side view of the plate of the variable angle blade plate inserted into the peri-articular portion of a given bone.

FIG. 2 is a depiction of the variable angle blade plate applied to a bone (in dotted lines), with screws 6 inserted.

Figure 3A:
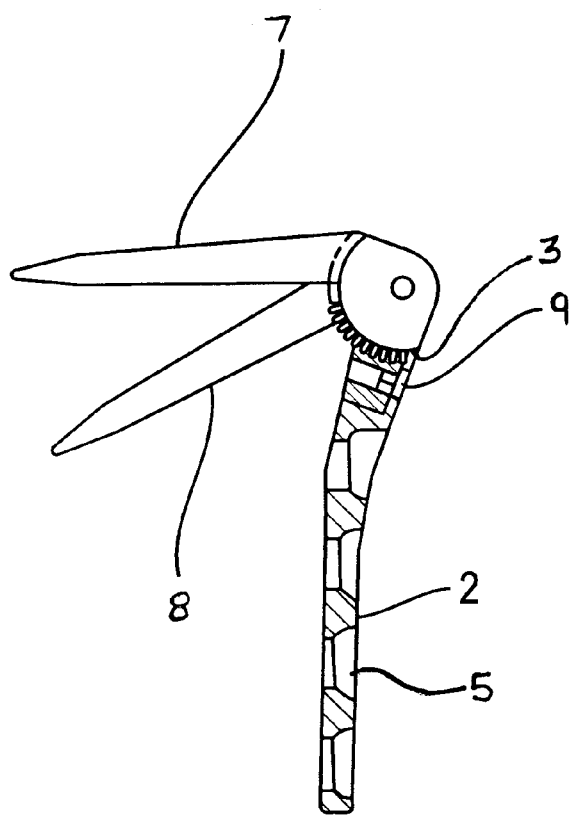
FIG. 3A shows a side view of a double blade variable angle blade plate according to a second embodiment of the invention.
Figure 3B:
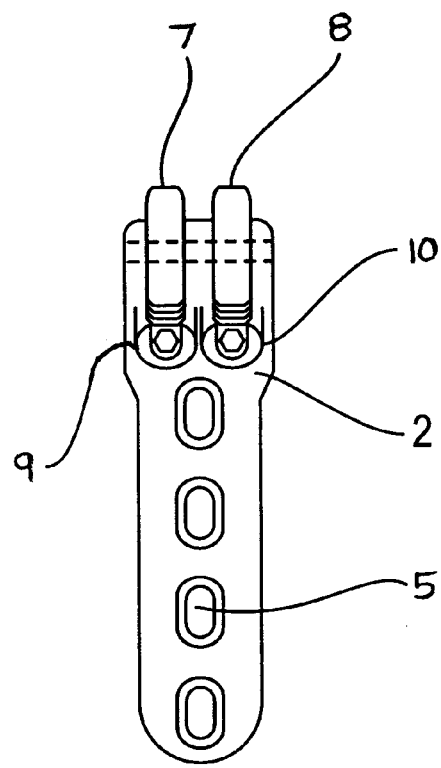
FIG. 3B shows a front view of the side plate portion of the double blade variable angle blade plate according to the second embodiment of the invention.
Figure 4:
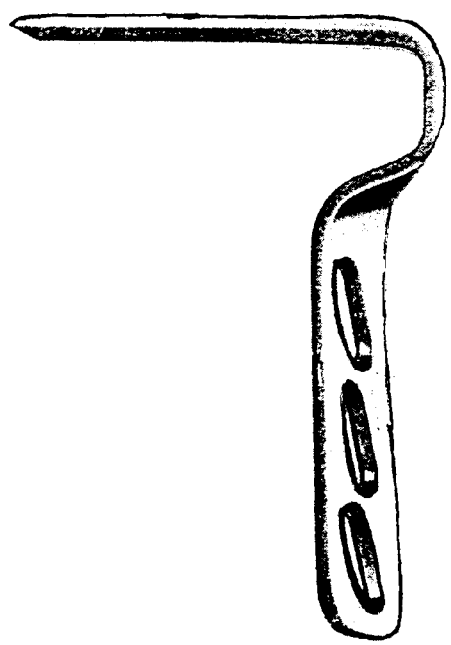
FIG. 4 shows a side view of a conventional one piece blade plate.
Figure 5:
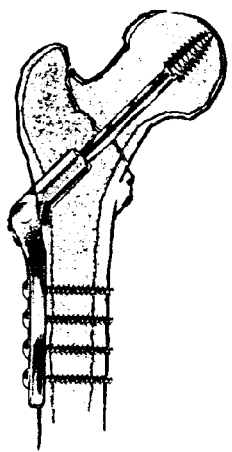
FIG. 5 shows a side view of a conventional two piece variable angle device.

In a second embodiment of the present invention, the variable angle blade plate is the same as that of the first embodiment—with like reference numerals depicting like structures in FIGS. 3A and 3B—with the exception that the plate includes two blade portions 7, 8 instead of a single blade portion, each blade portion 7, 8 having its own respective worm gear adjustment portion 9, 10.

In FIG. 3A, which shows a side view of the double blade variable angle blade plate, the blade portions 7, 8 are both tapered at the distal ends, with flat and curve edged surfaces, and are separately adjustable by using their respective worm gear adjustment portions 9, 10 (see FIG. 3B).

In operation, the blade portion 1 of the first embodiment of the variable angle blade plate, is inserted in the proximal portion of the bone, and by its flat and curve edged surface, gains fixation to the spongy or cancellous bone. The side plate portion 2 can be fixed to the bone by using a screw driver inserted in the worm gear adjustment portion 4 to turn the worm gear mechanism 3, thereby applying the side plate portion 2 to the outside diaphyseal portion of the bone, and fixing the side plate portion 2 to the bone with screws 6 inserted in the screw holes 5. If more or less angulation is required, the screw driver can be used to turn the worm gear mechanism 3 and change the angle of the plate, to easily accommodate these changes.

In the second embodiment of the present invention, the double blade variable angle blade plate is inserted in a similar manner as in the first embodiment, and depending on whether the anterior or posterior portion of the bone is depressed, the anterior or posterior blades are angled upwards to add additional support and fixation to this depressed segment of bone.

It is contemplated that numerous modifications may be made to the apparatus and procedure of the invention without departing from the spirit and scope of the invention as defined in the following claims.

What is claimed is:

1. An orthopedic plate which is adapted to be fixed to a fractured bone comprising:
   a first blade portion;
   a side plate portion; and
   a first adjustable angle mechanism connecting said first blade portion to said side plate portion.

2. The orthopedic plate of claim 1, wherein said first adjustable angle mechanism is a first worm gear mechanism.

3. The orthopedic plate of claim 1, further comprising:
   a plurality of screw holes disposed in said side plate portion for insertion of screws to fix said side plate portion to said bone.

4. The orthopedic plate of claim 2, wherein said first worm gear mechanism further comprises a first worm gear and a first worm gear adjustment portion, wherein upon insertion of a tool into said first worm gear adjustment portion, said first worm gear can be turned to change a first angle between said first blade portion and said side plate portion.

5. The orthopedic plate of claim 1, further comprising a second blade portion and a second adjustable angle mechanism connecting said second blade portion to said side plate portion.

6. The orthopedic plate of claim 5, wherein said second adjustable angle mechanism is a second worm gear mechanism.

7. The orthopedic plate of claim 6, wherein said second worm gear mechanism further comprises a second worm gear and a second worm gear adjustment portion, wherein upon insertion of a tool into said second worm gear adjustment portion, said second worm gear can be turned to change a second angle between said second blade portion and said side plate portion.

8. The orthopedic plate of claim 1, wherein said first blade portion comprises a flat and curve edged surface, and wherein said first blade portion is adapted to be inserted into a periarticular portion of the bone to gain fixation therein.

9. The orthopedic plate of claim 5, wherein said second blade portion comprises a flat and curve edged surface, and wherein said second blade portion is adapted to be inserted into a periarticular portion of the bone to gain fixation therein.

10. An orthopedic plate for treating orthopedic periarticular fractures and osteotomies, which is adapted to be fixed to a fractured bone comprising:
   a first blade portion;
   a side plate portion; and
   first means for adjusting a first angle between said first blade portion and said side plate portion.

11. The orthopedic plate of claim 10, further comprising a second blade portion and second means for adjusting a second angle between said second blade portion and said side plate portion.

12. The orthopedic plate of claim 11, further comprising:
   a plurality of screw holes disposed in said side plate portion for insertion of screws to fix said side plate portion to said bone.

13. An orthopedic plate for treating orthopedic periarticular fractures and osteotomies, which is adapted to be fixed to a fractured bone comprising:

a first blade portion having a flat and curve edged surface adapted for insertion into a periarticular portion of the bone to gain fixation therein;

a side plate portion; and a first mechanism for adjusting a first angle between said first blade portion and said side plate portion.

14. The orthopedic plate of claim 13, further comprising a second blade portion and a second mechanism for adjusting a second angle between said second blade portion and said side plate portion.

15. The orthopedic plate of claim 13, further comprising:

a plurality of screw holes disposed in said side plate portion for insertion of screws to fix said side plate portion to said bone.

* * * * *